United States Patent [19]

Sanderson et al.

[11] Patent Number: 5,191,130
[45] Date of Patent: * Mar. 2, 1993

[54] PROCESS FOR OLIGOMERIZING OLEFINS USING HALOGENATED PHOSPHOROUS-CONTAINING ACID ON MONTMORILLONITE CLAY

[75] Inventors: John R. Sanderson; John F. Knifton, both of Austin, Tex.

[73] Assignee: Texaco Chemical Company, White Plains, N.Y.

[*] Notice: The portion of the term of this patent subsequent to Mar. 17, 2009 has been disclaimed.

[21] Appl. No.: 807,342

[22] Filed: Dec. 16, 1991

[51] Int. Cl.$^5$ ............................. C07C 2/74; C07C 2/02
[52] U.S. Cl. ..................................... 585/255; 585/527
[58] Field of Search ................................ 585/255, 527

[56] References Cited

U.S. PATENT DOCUMENTS

| | | | |
|---|---|---|---|
| 2,586,852 | 2/1952 | Morrell | 502/81 |
| 2,713,560 | 7/1955 | Morrell | 502/81 |
| 2,732,408 | 1/1956 | Foote | 568/791 |
| 2,951,087 | 8/1960 | Hauser et al. | 502/62 |
| 3,412,039 | 11/1968 | Miller | 502/81 |
| 3,432,571 | 3/1969 | Noddings et al. | 585/300 |
| 3,459,815 | 8/1969 | Noddings et al. | 502/11 |
| 3,673,111 | 6/1972 | Hovarth et al. | 502/213 |
| 3,845,150 | 10/1974 | Yan et al. | 208/135 |
| 3,849,507 | 11/1974 | Zuech | 585/455 |
| 3,959,399 | 5/1976 | Bridwell et al. | 585/458 |
| 4,153,638 | 5/1979 | Bercik et al. | 585/526 |
| 4,263,465 | 4/1981 | Sheng et al. | 585/255 |
| 4,299,730 | 11/1981 | Sommer et al. | 502/63 |
| 4,351,980 | 9/1982 | Reusser et al. | 585/820 |
| 4,380,509 | 4/1983 | Sommer et al. | 502/439 |
| 4,456,779 | 6/1984 | Owen et al. | 585/415 |
| 4,480,142 | 10/1984 | Cobb | 585/465 |
| 4,482,772 | 11/1984 | Tabak | 585/255 |
| 4,531,014 | 7/1985 | Gregory et al. | 585/415 |
| 4,604,491 | 8/1986 | Dressler et al. | 585/26 |
| 4,675,463 | 6/1987 | Glivichy et al. | 585/514 |
| 4,808,559 | 2/1989 | Sommer et al. | 502/63 |
| 4,827,064 | 5/1989 | Wu | 585/10 |
| 4,879,425 | 11/1989 | Kukes et al. | 585/350 |
| 4,946,815 | 8/1990 | Chao et al. | 585/529 |
| 5,097,085 | 3/1992 | Sanderson et al. | 585/255 |

FOREIGN PATENT DOCUMENTS

0353813 2/1990 European Pat. Off. .
1489646 10/1977 United Kingdom .

OTHER PUBLICATIONS

Kuliev et al., "Preparation of High-Viscosity Synthetic Lubricants Using an Aluminosilicate Catalyst," Institute of Petrochemical Processes of the Academy of Sciences of the Azerbaizhen SSR, Azerbaidzhanskoe, Neftiano, Khoziastvo, 1983, No. 4, pp.40-43.

Chaudhuri and Sharma, "Some Novel Aspects of the Dimerization of α-Methyl-styrene with Acidic Ion-Exchange Resins, Clays, and other Acidic Materials as Catalysts," Ind. Eng. Res., vol. 28, pp. 1757-1763 (1989).

Purnell, "Catalysis by Ion-Exchanged Montmorillonites," Catalysis Letters, 5 (1990), pp. 203-210.

Figueras, "Pillared Clays as Catalysts," Catal. Rev.-Sci. Eng., 30(3) pp. 457-499 (1988).

Friedlander, "Organized Polymerization.I. Olefins on a Clay Surface." Journal of Polymer Science: Part C, No. 4, pp. 1291-1301.

Friedlander et al., "Organized Polymerization III, Monomers Intercalated in Montmorillonite," Polymer Letters, vol. 2, 475-479.

"Intercalated Catalysts and Pillared Clays," Process Evaluation/Research Planning Report, Chem Systems, Catalysts: Selected Developments, 84-3, pp. 239-249 (Dec. 1985).

Bolan, "Synthetic Lubricant Base Stocks," Process Economics Program Report No. 125A by SRI International, Apr. 1989 and Supplement A, Sep. 1989.

"Synthetic Lubricants from Internal Olefins," Process Evaluation/Research Planning Report by Chem Systems, 84-Q-1, pp. 17-45.

Adams, "Synthetic Organic Chemistry Using Pillared, Cation-Exchanged and Acid-Treated Montmorillonite Catalysts—A Review," Applied Clay Science, 2 (1987) pp. 309-342.

Adams et al. "Clays as Selective Catalysts in Organic Synthesis," Journal of Inclusion Phenomena, vol. 5 (1987), pp. 663-674.

Primary Examiner—Patrick P. Garvin
Assistant Examiner—E. D. Irzinski
Attorney, Agent, or Firm—Jack H. Park; Kenneth R. Priem; Russell R. Stolle

[57] ABSTRACT

An improved process is disclosed for preparing synthetic lubricant base stocks. Synthetic lubricant base stocks are prepared in good yield by oligomerizing linear olefins using montmorillonite clays which have a halogenated phosphorous- containing acid deposited thereon.

20 Claims, No Drawings

PROCESS FOR OLIGOMERIZING OLEFINS USING HALOGENATED PHOSPHOROUS-CONTAINING ACID ON MONTMORILLONITE CLAY

BACKGROUND OF THE INVENTION

1. Field of the Invention

The invention relates to the preparation of synthetic lubricant base stocks, and more particularly to synthetic lubricant base stocks made by oligomerizing linear olefins.

2. Description of Related Methods

Synthetic lubricants are prepared from man-made base stocks having uniform molecular structures and, therefore, well-defined properties that can be tailored to specific applications. Mineral oil base stocks, on the other hand, are prepared from crude oil and consist of complex mixtures of naturally occurring hydrocarbons. The higher degree of uniformity found in synthetic lubricants generally results in superior performance properties. For example, synthetic lubricants are characterized by excellent thermal stability. As automobile engines are reduced in size to save weight and fuel, they run at higher temperatures, therefore requiring a more thermally stable oil. Because lubricants made from synthetic base stocks have such properties as excellent oxidative/thermal stability, very low volatility, and good viscosity indices over a wide range of temperatures, they offer better lubrication and permit longer drain intervals, with less oil vaporization loss between oil changes.

Synthetic base stocks may be prepared by oligomerizing internal and alpha-olefin monomers to form a mixture of dimers, trimers, tetramers, and pentamers, with minimal amounts of higher oligomers. The unsaturated oligomer products are then hydrogenated to improve their oxidative stability. The resulting synthetic base stocks have uniform isoparaffinic hydrocarbon structures similar to high quality paraffinic mineral base stocks, but have the superior properties mentioned due to their higher degree of uniformity.

Synthetic base stocks are produced in a broad range of viscosity grades. It is common practice to classify the base stocks by their viscosities, measured in centistokes (cSt) at 100° C. Those base stocks with viscosities less than or equal to about 4 cSt are commonly referred to as "low viscosity" base stocks, whereas base stocks having a viscosity in the range of around 40 to 100 cSt are commonly referred to as "high viscosity" base stocks. Base stocks having a viscosity of about 4 to about 8 cSt are referred to as "medium viscosity" base stocks. The low viscosity base stocks generally are recommended for low temperature applications. Higher temperature applications, such as motor oils, automatic transmission fluids, turbine lubricants, and other industrial lubricants, generally require higher viscosities, such as those provided by medium viscosity base stocks (i.e. 4 to 8 cSt grades). High viscosity base stocks are used in gear oils and as blending stocks.

The viscosity of the base stocks is determined by the length of the oligomer molecules formed during the oligomerization reaction. The degree of oligomerization is affected by the catalyst and reaction conditions employed during the oligomerization reaction. The length of the carbon chain of the monomer starting material also has a direct influence on the properties of the oligomer products. Fluids prepared from short-chain monomers tend to have low pour points and moderately low viscosity indices, whereas fluids prepared from long-chain monomers tend to have moderately low pour points and higher viscosity indices. Oligomers prepared from long-chain monomers generally are more suitable than those prepared from shorter-chain monomers for use as medium viscosity synthetic lubricant base stocks.

One known approach to oligomerizing long-chain olefins to prepare synthetic lubricant base stocks is to contact the olefin with boron trifluoride together with a promotor at a reaction temperature sufficient to effect oligomerization of the olefin. See, for example, co-assigned U.S. Pat. Nos. 4,400,565; 4,420,646; 4,420,647; and 4,434,308. However, boron trifluoride gas ($BF_3$) is a pulmonary irritant, and breathing the gas or fumes formed by hydration of the gas with atmospheric moisture poses hazards preferably avoided. Additionally, the disposal/neutralization of $BF_3$ raises environmental concerns. Thus, a method for oligomerizing long-chain olefins using a non-hazardous, non-polluting catalyst would be a substantial improvement in the art.

Kuliev et al. attempted to prepare synthetic lubricants by oligomerizing long-chain ($C_9$–$C_{14}$) olefins using non-hazardous and non-polluting acidic clays comprising sulfuric and hydrochloric acid-activated bentonites from the Azerbaidzhan SSR. See Kuliev, Abasova, Gasanova, Kotlyarevskaya, and Valiev, "Preparation of High-Viscosity Synthetic Lubricants Using an Aluminosilicate Catalyst," Institute of Petrochemical Processes of the Academy of Sciences of the Azerbaidzhan SSR, Azer. Neft. Khoz., 1983, No. 4, pages 40–43. However, Kuliev et al. concluded that "it was not possible to prepare viscous or high-viscosity oils by olefin polymerization over an aluminosilicate catalyst" and that "hydrogen redistribution reactions predominate with formation of aromatic hydrocarbon, coke, and paraffinic hydrocarbon." Gregory et al., on the other hand, used Wyoming bentonite to oligomerize shorter-chain olefins. (See U.S. Pat. No. 4,531,014.) However, like Kuliev et al., they also were unable to obtain a product high in dimer, trimer and tetramer, and low in disproportionation products.

Applicants have discovered, surprisingly, that a high conversion of olefin to oligomer may be obtained by contacting the olefin with a catalyst prepared by depositing a halogenated phosphorous-containing acid on a substrate comprising montmorillonite clay. Applicants have further discovered that where the halogenated phosphorous-containing acid is a fluorinated phosphorous-containing acid, the process of the present invention results in a very high percentage of trimer and higher oligomers, i.e., a very low dimer to trimer ratio. A high proportion of trimer and higher oligomers is particularly desirable when preparing a synthetic lubricant base stock from decene. In the absence of the low dimer to trimer ratio obtained using the present invention, substantial decene dimer must be recycled and further oligomerized to prepare enough oligomers having sufficient molecular weight to obtain base stocks suitable for synthetic lubricants. In addition to being excellent catalysts, the treated clays of the present invention are less hazardous and more easily handled than $BF_3$.

SUMMARY OF THE INVENTION

The invention relates to a process for the preparation of oligomers, comprising the following steps: (1) depositing a halogenated, phosphorous-containing acid on a substrate comprising montmorillonite clay; and (2) contacting at elevated temperature (a) linear olefins containing from 10 to 24 carbon atoms with (b) a catalytically effective amount of the montmorillonite clay having said acid deposited thereon. The invention further relates to a process for the preparation of oligomer base stocks having a low dimer to trimer ratio, comprising the following steps: (1) depositing a fluorinated, phosphorous-containing acid on a substrate comprising montmorillonite clay; and (2) contacting linear olefins containing from 10 to 24 carbon atoms with a catalytically effective amount of the montmorillonite clay having said acid deposited thereon, at a temperature of about 120° C. to about 250° C. The invention also relates to a process for the preparation of oligomer base stocks having a low dimer to trimer ratio, comprising contacting linear olefins containing from 10 to 24 carbon atoms with a catalyst comprising montmorillonite clay having fluorophosphoric acid or difluorophosphoric deposited thereon, at a temperature of about 120° to about 250° C. and at a pressure of about atmospheric to about 1000 psig.

DESCRIPTION OF THE PREFERRED EMBODIMENTS

Applicants have discovered that an improved conversion of olefin to oligomer may be obtained where montmorillonite clays are treated with a halogenated, phosphorous-containing acid prior to use as an oligomerization catalyst. Applicants have further discovered that where the halogenated, phosphorous-containing acid is a fluorinated, phosphorous-containing acid, the process of the present invention results in a very high percentage of trimer and higher oligomers, i.e., a very low dimer to trimer ratio.

The olefin monomer feed stocks used in the present invention may be selected from compounds comprising (1) alphaolefins having the formula $R''CH=CH_2$, where $R''$ is an alkyl radical of 8 to 22 carbon atoms, and (2) internal olefins having the formula $RCH=CHR'$, where R and R' are the same or different alkyl radicals of 1 to 21 carbon atoms, provided that the total number of carbon atoms in any one olefin shall be within the range of 10 to 24, inclusive. Mixtures of internal and alpha-olefins may be used, as well as mixtures of olefins having different numbers of carbon atoms, provided that the total number of carbon atoms in any one olefin shall be within the range of 10 to 24, inclusive. The alpha and internal-olefins to be oligomerized in this invention may be obtained by processes well-known to those skilled in the art and are commercially available.

The oligomerization reaction may be represented by the following general equation:

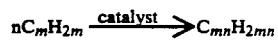

where n represents moles of monomer and m represents the number of carbon atoms in the monomer. Thus, the oligomerization of 1-decene may be represented as follows:

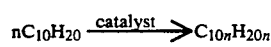

The reaction occurs sequentially. Initially, olefin monomer reacts with olefin monomer to form dimers. Most of the dimers that are formed then react with additional olefin monomer to form trimers, and so on. This results in an oligomer product distribution that varies with reaction time. As the reaction time increases, the olefin monomer conversion increases, and the selectivities for the heavier oligomers increase. Generally, each resulting oligomer contains one double bond.

The oligomers are prepared using certain silica-alumina clays, also called aluminosilicates, which have been treated with a halogenated, phosphorous-containing acid. Silica-alumina clays primarily are composed of silicon, aluminum, and oxygen, with minor amounts of magnesium and iron in some cases. Variations in the ratios of these constituents, and in their crystal lattice configurations, result in some fifty separate clays, each with its own characteristic properties.

One class of silica-alumina clays comprises smectite clays. Smectite clays have a small particle size and unusual intercalation properties that afford them a high surface area. Smectites comprise layered sheets of octahedral sites between sheets of tetrahedral sites, where the distance between the layers can be adjusted by swelling, using an appropriate solvent. Three-layered sheet-type smectites include montmorillonites. The montmorillonite structure may be represented by the following formula:

Where M represents the interlamellar (balancing) cations, normally sodium or lithium; and x, y and n are integers.

Montmorillonite clays may be acid-activated by such mineral acids as sulfuric acid and hydrochloric acid. Mineral acids activate montmorillonites by attacking and solubilizing structural cations in the octahedral layers. This opens up the clay structure and increases surface area. These acid-treated clays act as strong Bronsted acids. Illustrative examples of commercially available acid-treated clays include Engelhard Corporation's Grade F24, having a moisture content of 12 wt. %, a residual acidity of 16 mg KOH/g, and a surface area of 350 m$^2$/g; Grade F124, having a moisture content of 4 wt. %, a residual acidity of 14 mg KOH/g, and a surface area of 350 m$^2$/g; Grade F13, having a moisture content of 12 wt. %, a residual acidity of 15 mg KOH/g, and a surface area of 300 m$^2$/g; Grade F113, having a moisture content of 4 wt. %, a residual acidity of 15 mg KOH/g, and a surface area of 300 m$^2$/g; and Grade F224, having virtually no moisture, and having a residual acidity of 5 mg KOH/g, and a surface area of 350 m$^2$/g.

Applicants have discovered that a high conversion of olefin to oligomer may be obtained by contacting the olefin feed with a catalyst prepared by depositing a halogenated, phosphorous-containing acid on a substrate comprising a montmorillonite clay. The montmorillonite substrate may comprise a neutral to basic clay (i.e. having a pH of about 7 or greater), or one that has previously been acid treated as described above. Preferably, the clay has not been treated with an acid prior to its use as a substrate for the halogenated, phosphorous-containing acid, and has a residual acidity of less than about 1 mg KOH/g. An especially preferred clay is Engelhard's Grade F2C, having a moisture content at 220° F. of 15 wt. % and a pH of 7.5. Another suitable commercially available clay is Engelhard's Desiccate-25.

In the present invention, the clay is treated with halogenated, phosphorous-containing acid prior to running the oligomerization reaction. It is preferred that the halogenated, phosphorous-containing acid to be deposited on the montmorillonite clay be a fluorinated, phosphorous-containing acid, such as, for example, the fluorinated derivatives of the following acids: hypophosphorous acid, hypophosphoric acid, orthophosphoric acid, metaphosphoric acid, and polyphosphoric acid. It is especially preferred that the halogenated, phosphorous-containing acid to be deposited on the montmorillonite clay be difluorophosphoric acid or fluorophosphoric acid.

The clay should be added to a solution of about 2 to about 100 wt. %, preferably from about 5 to about 20 wt. %, halogenated, phosphorous-containing acid in water or organic solvent, such as acetone or alcohol. The ratio of clay to halogenated, phosphorous-containing acid solution should be sufficient to provide a catalyst having a quantity of phosphorous deposited thereon ranging from about 0.1 to about 20 wt. %, preferably about 1 to about 5 wt. %. The clay should remain in the halogenated, phosphorous-containing acid solution for a period of time and under agitation to the extent necessary to meet these requirements, and then filtered and dried. Optionally, the filtered clay having said acid deposited thereon may be washed with distilled water and then dried, preferably under mild conditions.

Preferably, the halogenated, phosphorous-containing acid treated catalyst is heat treated before running the reaction. Applicants found that heat treatment of the catalyst prior to running the oligomerization reaction causes the catalyst to be more active and produce a higher olefin conversion. Additionally, clays heat treated in this manner are more stable, remaining active during the oligomerization reaction for a longer period of time. The clays may be heat treated at temperatures in the range of about 50° C. to 400° C., with or without the use of a vacuum. A more preferred temperature range is 50° C. to 300° C. Optionally, an inert gas may be used during heat treatment as well. Preferably, the clay should be heat treated under conditions and for a length of time which will reduce the water content of the clay to approximately 1 to 2 wt. % or less.

The oligomerization reaction may be carried out either batchwise, in a stirred slurry reactor, or continuously, in a fixed bed continuous flow reactor. The catalyst concentration should be sufficient to provide the desired catalytic effect. The temperatures at which the oligomerization may be performed are between about 50° C. and 300° C., with the preferred range being about 120° C. to 250° C., and the especially preferred range being about 160° C. to 180° C., for optimum conversion. However, to obtain a lower dimer to trimer ratio, it is preferred that the oligomerization be performed at a temperature in the range of about 135° C. to about 160° C., and especially preferred that the temperature be in the range of about 135° C. to about 145° C.

At reaction temperatures of about 200° C. or greater, the amount of unsaturation remaining in the products of the oligomerization reaction may decrease, thus reducing the degree of hydrogenation necessary to remove unsaturation from the base stocks. However, at temperatures above 200° C., the olefin conversion may decrease and the dimer to trimer ratio will increase. Applicants have found that the addition of a hydrocarbon containing a tertiary hydrogen, such as methylcyclohexane, may further reduce the amount of unsaturation present in the base stocks. One skilled in the art may choose the reaction conditions most suited to the results desired for a particular application. The reaction may be run at pressures of from 0 to 1000 psig.

Following the oligomerization reaction, the unsaturated oligomers may be hydrogenated to improve their thermal stability and to guard against oxidative degradation during their use as lubricants. The hydrogenation reaction for 1-decene oligomers may be represented as follows:

$$C_{10n}H_{20n} + H_2 \xrightarrow{\text{catalyst}} C_{10n}H_{(20n+2)}$$

where n represents moles of monomer used to form the oligomer. Hydrogenation processes known to those skilled in the art may be used to hydrogenate the oligomers. A number of metal catalysts are suitable for promoting the hydrogenation reaction, including nickel, platinum, palladium, copper, and Raney nickel. These metals may be supported on a variety of porous materials such as kieselguhr, alumina, or charcoal, or they may be formulated into a bulk metal catalyst. A particularly preferred catalyst for this hydrogenation is a nickel-copper-chromia catalyst described in U.S. Pat. No. 3,152,998, incorporated by reference herein. Other U.S. patents disclosing known hydrogenation procedures include U.S. Pat. Nos. 4,045,508; 4,013,736; 3,997,622; and 3,997,621.

Unreacted monomer may be removed either prior to or after the hydrogenation step. Optionally, unreacted monomer may be stripped from the oligomers prior to hydrogenation and recycled to the catalyst bed for oligomerization. The removal or recycle of unreacted monomer or, if after hydrogenation, the removal of non-oligomerized alkane, should be conducted under mild conditions using vacuum distillation procedures known to those skilled in the art. Similarly, where the olefin feed is decene, it also may be necessary to remove or recycle decene dimers in order to obtain base stocks suitable for synthetic lubricants. The extent of removal or recycle of decene dimers is minimized by the preferred embodiments of the present invention. For example, Applicants have demonstrated that when decene is oligomerized in the presence of difluorophosporic acid or fluorophosphoric acid catalysts at a temperature up to about 180° C., dimer to trimer+ ratios less than 0.80 are routinely observed. At slightly lower temperatures, Applicants obtained ratios of dimers to trimers and higher oligomers of less than about 0.70, and as low as less than 0.50.

Distillation at temperatures exceeding 250° C. may cause the oligomers to break down in some fashion and come off as volatiles. Preferably, therefore, the reboiler or pot temperature should be kept at or under about 225° C. when stripping out the monomer. Procedures known by those skilled in the art to be alternatives to vacuum distillation also may be employed to separate unreacted components from the oligomer.

The invention will be further illustrated by the following examples, which are given by way of illustration and not as limitations on the scope of this invention.

EXAMPLES

In the examples detailed in the table below, the following procedures were used:

Preparation of Catalysts

A. Difluorophosphoric acid on Grade F2C

To 100 g of montmorillonite clay (Engelhard Clay Grade F2C powder) was added, under nitrogen, a solution of difluorophosphoric acid (10.0 g) in distilled water (100 cc). The mixture was stirred under nitrogen for 24 hours. The white solid product was recovered by filtration, washed with distilled water until the washings were Ph neutral, and dried in vacuo at 40° C. for 4 hours, and then at 150° C. overnight.

Analysis of the product showed:
% Water=1.25.
Acidity=0.07 meg/g.

B. Difluorophosphoric acid on Desiccate-25

To 200 g of clay granules (Engelhard Desiccate-25) was added, under nitrogen, a solution of difluorophosphoric acid (20 g) in distilled water (200 g). The mixture was stirred under nitrogen for 24 hours. The white solids were recovered by filtration, washed with distilled water until the washings were pH neutral, and dried in vacuo at 40° C. for 4 hours, and then at 150° C. overnight.

Analysis of the product showed:
% Water=1.26.
Acidity=0.053 meg/g.

Olefin Oligomerization

Olefin and catalyst were charged to a flask equipped with a stirrer, thermometer, heating mantle, condenser, and nitrogen purge. The mixture was heated to the desired temperature, for the desired time, with vigorous stirring. At the end of the reaction, the mixture was cooled to ambient temperature, filtered with suction, and the liquid effluent analyzed by liquid chromatography. The results are shown the table below.

lytically effective amount of the montmorillonite clay having said acid deposited thereon.

2. The process of claim 1, wherein the montmorillonite clay has a residual acidity of less than about 1 mg KOH/g prior to treatment with the halogenated, phosphorous-containing acid.

3. The process of claim 1, wherein the montmorillonite clay has a pH of about 7 or greater prior to treatment with the halogenated, phosphorous-containing acid.

4. The process of claim 1, wherein the olefin and montmorillonite clay are contacted at a temperature in the range of about 50° C. to about 300° C. and at a pressure of about atmospheric to about 1000 psig.

5. The process of claim 1, wherein the halogenated, phosphorous-containing acid is a halogenated derivative of hypophosphorous acid, hypophosphoric acid, orthophosphoric acid, metaphosphoric acid, or polyphosphoric acid.

6. The process of claim 1, wherein the halogenated, phosphorous-containing acid is a halogenated derivative of orthophosphoric acid.

7. The process of claim 1, wherein the halogenated, phosphorous-containing acid has a phosphorous content of up to about 20 wt. %.

8. A process for the preparation of oligomer base stocks having a low dimer to trimer ratio, comprising the following steps: (1) depositing a fluorinated, phosphorous-containing acid on a substrate comprising montmorillonite clay; and (2) contacting linear olefins containing from 10 to 24 carbon atoms with a catalytically effective amount of the montmorillonite clay having said acid deposited thereon, at a temperature of about 120° C. to about 250° C.

9. The process of claim 8, wherein the fluorinated, phosphorous-containing acid has a phosphorous content of up to about 20 wt. %.

10. The process of claim 8, wherein the montmorillonite clay has a residual acidity of less than about 1 mg KOH/g prior to treatment with the fluorinated, phosphorous-containing acid.

11. The process of claim 8, wherein the temperature is about 135° C. to about 160° C.

12. The process of claim 8, wherein the temperature is about 135° C. to about 145° C.

13. The process of claim 8, wherein the fluorinated, phosphorous-containing acid is a fluorinated derivative of hypophosphorous acid, hypophosphoric acid, ortho-

| Ex. No. | Catalyst | Amount of Catalyst (g) | Olefin | Amount of Olefin (g) | Temp. (°C.) | Time (Hr) | Con. (%) | D/T + Ratio |
|---|---|---|---|---|---|---|---|---|
| 1 | DFPA on Clay Grade 2C | 10 | 14α | 100 | 160 | 5.0 | 82.2 | 0.80 |
| 2 | DFPA on Clay Grade 2C | 10 | 10α | 100 | 140 | 4.0 | 82.5 | 0.45 |
| 3 | DFPA on Clay Grade 2C | 10 | 10α | 100 | 160 | 5.0 | 88.1 | 0.61 |
| 4 | DFPA on Clay Grade 2C | 10 | 10α | 100 | 180 | 4.0 | 90.6 | 0.59 |
| 5 | DFPA on Clay Grade 2C | 10 | 10α | 100 | 140 | 8.0 | 84.4 | 0.55 |
| 6 | HCl on Clay Grade 2C | 10 | 10α | 100 | 160 | 5.0 | 72.6 | 0.94 |
| 7 | None | — | 10α | 100 | 160 | 5.0 | 00.0 | — |
| 8 | Desiccate-25 | 10 | 10α | 100 | 160 | 5.0 | 55.9 | 0.83 |
| 9 | DFPA on Desiccate-25 | 10 | 10α | 100 | 140 | 5.0 | 80.6 | 0.59 |
| 10 | DFPA on Desiccate-25 | 10 | 10α | 100 | 160 | 5.0 | 87.2 | 0.71 |
| 11 | DFPA on Desiccate-25 | 10 | 10α | 100 | 180 | 4.0 | 89.0 | 0.74 |
| 12 | Clay-2C | 10 | 10α | 100 | 160 | 5.0 | 57.9 | 1.14 |
| 13 | FPA on Clay Grade 2C | 10 | 10α | 100 | 140 | 6.0 | 82.6 | 0.53 |
| 14 | FPA on Clay Grade 2C | 10 | 10α | 100 | 160 | 5.0 | 86.5 | 0.67 |
| 15 | FPA on Clay Grade 2C | 10 | 10α | 100 | 180 | 4.0 | 87.8 | 0.75 |

DFPA = Difluorophosphoric acid; HCL = hydrochloric acid; FPA = fluorophosphoric acid; Con. = Olefin conversion; D = Dimer; T + = Trimer + Tetramer + Pentamer, etc.

We claim:

1. A process for the preparation of oligomers, comprising the following steps: (1) depositing a halogenated, phosphorous-containing acid on a substrate comprising montmorillonite clay; and (2) contacting under effective oligomerization conditions (a) linear olefins containing from 10 to 24 carbon atoms with (b) a cataphosphoric acid, metaphosphoric acid, or polyphosphoric acid.

14. The process of claim 8, wherein the fluorinated, phosphorous-containing acid is fluorophosphoric acid or difluorophosphoric acid.

15. The process of claim 8, wherein the montmorillonite clay having said fluorinated, phosphorous-containing acid deposited thereon has a phosphorous content of about 1 to about 5 wt. %.

16. A process for the preparation of oligomer base stocks having a low dimer to trimer ratio, comprising contacting linear olefins containing from 10 to 24 carbon atoms with a catalyst comprising montmorillonite clay having fluorophosphoric acid or difluorophosphoric deposited thereon, at a temperature of about 120° C. to about 250° C. and at a pressure of about atmospheric to about 1000 psig.

17. The process of claim 16, further comprising the step of recovering oligomers in a ratio of dimers to trimer and higher oligomers of less than about 0.80.

18. The process of claim 16, wherein the temperature is about 135° C. to about 160° C.

19. The process of claim 16, wherein the temperature is about 135° C. to about 145° C.

20. The process of claim 16, further comprising the step of recovering oligomers in a ratio of dimers to trimer and higher oligomers of less than about 0.70.

* * * * *